(12) United States Patent
Nam et al.

(10) Patent No.: US 11,360,063 B2
(45) Date of Patent: Jun. 14, 2022

(54) QUANTITATIVE ANALYSIS METHOD FOR HIGH MOLECULAR WEIGHT ANTIOXIDANT

(71) Applicant: LG CHEM, LTD., Seoul (KR)

(72) Inventors: Moon Ja Nam, Daejeon (KR); Byoung Hyoun Kim, Daejeon (KR); Min Jeong Lee, Daejeon (KR)

(73) Assignee: LG Chem, Ltd.

( * ) Notice: Subject to any disclaimer, the term of this patent is extended or adjusted under 35 U.S.C. 154(b) by 645 days.

(21) Appl. No.: 16/346,945

(22) PCT Filed: Jul. 23, 2018

(86) PCT No.: PCT/KR2018/008259
§ 371 (c)(1),
(2) Date: May 2, 2019

(87) PCT Pub. No.: WO2019/054623
PCT Pub. Date: Mar. 21, 2019

(65) Prior Publication Data
US 2020/0057035 A1    Feb. 20, 2020

(30) Foreign Application Priority Data

Sep. 12, 2017    (KR) .................. 10-2017-0116612

(51) Int. Cl.
*G01N 30/88*    (2006.01)
*C08K 5/00*    (2006.01)
(Continued)

(52) U.S. Cl.
CPC ............. *G01N 30/88* (2013.01); *C08K 5/005* (2013.01); *C08K 5/3437* (2013.01);
(Continued)

(58) Field of Classification Search
CPC .......... G01N 30/88; G01N 1/38; G01N 30/68; G01N 2001/386; G01N 2030/025;
(Continued)

(56) References Cited

U.S. PATENT DOCUMENTS

2008/0262136 A1    10/2008  Akermark et al.
2011/0186328 A1    8/2011   Easter
(Continued)

FOREIGN PATENT DOCUMENTS

CN    102906824 A    1/2013
CN    104409178 A    3/2015
(Continued)

OTHER PUBLICATIONS

Search report from International Application No. PCT/KR2018/008259, dated Nov. 7, 2018.
(Continued)

*Primary Examiner* — Jennifer Wecker
*Assistant Examiner* — Michael Paul Shimek
(74) *Attorney, Agent, or Firm* — Lerner, David, Littenberg, Krumholz & Mentlik, LLP

(57) ABSTRACT

A method for analyzing an antioxidant content contained in a semiconductive material for a cable, which includes an amine-based antioxidant. The method can provide an accurate quantitative analysis value obtained by a comparison with the actual amount used, through gas chromatography (GC)/a flame ionization detector (FID).

6 Claims, 3 Drawing Sheets

(51) Int. Cl.
*C08K 5/3437* (2006.01)
*C08L 23/08* (2006.01)
*G01N 1/38* (2006.01)
*G01N 30/68* (2006.01)
*G01N 30/02* (2006.01)
*G01N 33/00* (2006.01)

(52) U.S. Cl.
CPC ............ *C08L 23/0853* (2013.01); *G01N 1/38* (2013.01); *G01N 30/68* (2013.01); *C08L 2203/20* (2013.01); *C08L 2312/00* (2013.01); *G01N 2001/386* (2013.01); *G01N 2030/025* (2013.01); *G01N 2033/0095* (2013.01)

(58) Field of Classification Search
CPC ........... G01N 2033/0095; G01N 30/02; G01N 2030/884; C08K 5/005; C08K 5/3437; C08L 23/0853; C08L 2203/20; C08L 2312/00
See application file for complete search history.

(56) References Cited

U.S. PATENT DOCUMENTS

| | | |
|---|---|---|
| 2011/0215278 A1 | 9/2011 | Easter |
| 2011/0288216 A1 | 11/2011 | Ayabe et al. |
| 2015/0315355 A1 | 11/2015 | Seven et al. |

FOREIGN PATENT DOCUMENTS

| | | | |
|---|---|---|---|
| EP | 2392616 A1 | | 12/2011 |
| JP | H06279319 A | | 10/1994 |
| JP | H0831241 A | | 2/1996 |
| JP | H08134275 A | | 5/1996 |
| JP | 2003315323 A | | 11/2003 |
| JP | 2010196033 A | | 9/2010 |
| JP | 2013519193 A | | 5/2013 |
| JP | 2013534021 A | | 8/2013 |
| JP | 2015141059 A | | 8/2015 |
| JP | 2016173328 A | * | 9/2016 |
| JP | 2016173328 A | | 9/2016 |
| KR | 19920012911 | | 7/1992 |
| KR | 20000002831 A | | 1/2000 |
| KR | 20070109317 A | | 11/2007 |
| KR | 20110020539 A | | 3/2011 |
| KR | 20120010884 A | | 2/2012 |
| KR | 20150097524 A | | 8/2015 |
| KR | 20160032741 A | | 3/2016 |
| WO | 2008144086 A1 | | 11/2008 |
| WO | 2014040237 A1 | | 3/2014 |

OTHER PUBLICATIONS

Li, Bo., et al., "Determination of Polymer Additives-Antioxidants, Ultraviolet Stabilizers, Plastsicizers and Photoinitiators in Plastic Food Package and Acelerated Solvent Extraction Coupled with High-Performance Liquid Chromatography." Journal of Chromatographic Science, vol. 53, No. 6, (revised Sep. 7, 2014; Advance Access publication Dec. 3, 2014), pp. 1026-1035.

Vimalasiri, P. A. D. T., et al., "Chromatographic Analsyis of Elastomer Antidegradants and Accelerators." Journal of Chromatography, Vo. 300, pp. 303-355.

"Rubber-Identification of antidegradants by gas chromatography/mass spectrometry." ISO (International Organization for Standardization), ISO 10638:2010, Ediition 1, Publication date Jul. 2010.

Extended European Search Report with Written Opinion for U.S. Appl. No. 18/856,898 4 dated Dec. 2, 2019, 8 pages.

Marcato et al., "Microwave-assisted extraction by fast sample preparation for the systematic analysis of additives in polyolefins by high-performance liquid chromatography," Journal of Chromatography A, Feb. 1, 2000, pp. 285-300., vol. 869, No. 1-2, , Elsevier, Amsterdam, NL, XP004186572.

Moller, et al., "Comparison of extraction methods for sampling of low molecular compounds in polymers degraded during recycling," European Polymer Journal, Jun. 1, 2008, pp. 1583-1593, vol. 44, No. 6, Pergamon Press Ltd. Oxford, GB, XP022703239.

Cai DL, Hua JL, Zhang YL, Zhang JY, Xie HY. Determination of BHT and BHA in EVA Material by GC-MS. Technology & Development of Chemical Industry. Apr. 2011; vol. 40 (4):pp. 30-32.

Fracasso ME, Franceschetti P, Mossini E, Tieghi S, Perbellini L, Romeo L. Exposure to mutagenic airborne particulate in a rubber manufacturing plant. Mutation Research/Genetic Toxicology and Environmental Mutagenesis. Apr. 26, 1999;441(1):43-51.

Search Report from Chinese Office Action for Application No. 2018800043554 dated Aug. 28, 2020; 3 pages.

* cited by examiner

[Fig. 1]
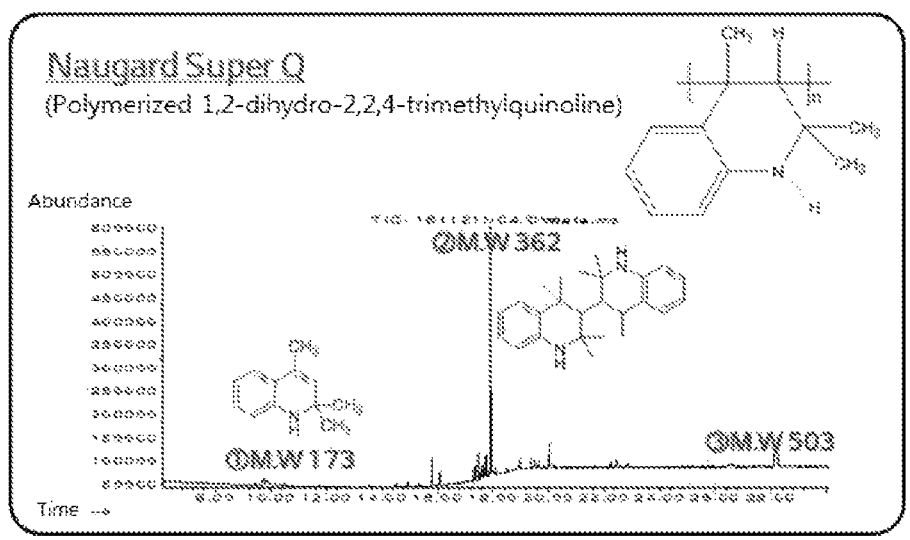
[Fig. 2]
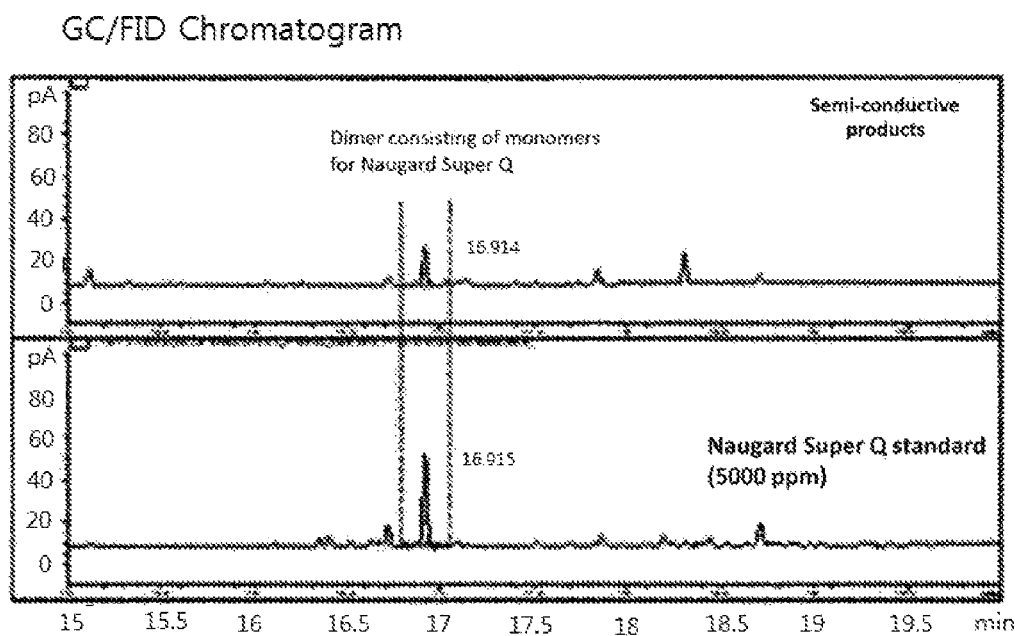

[Fig. 3]
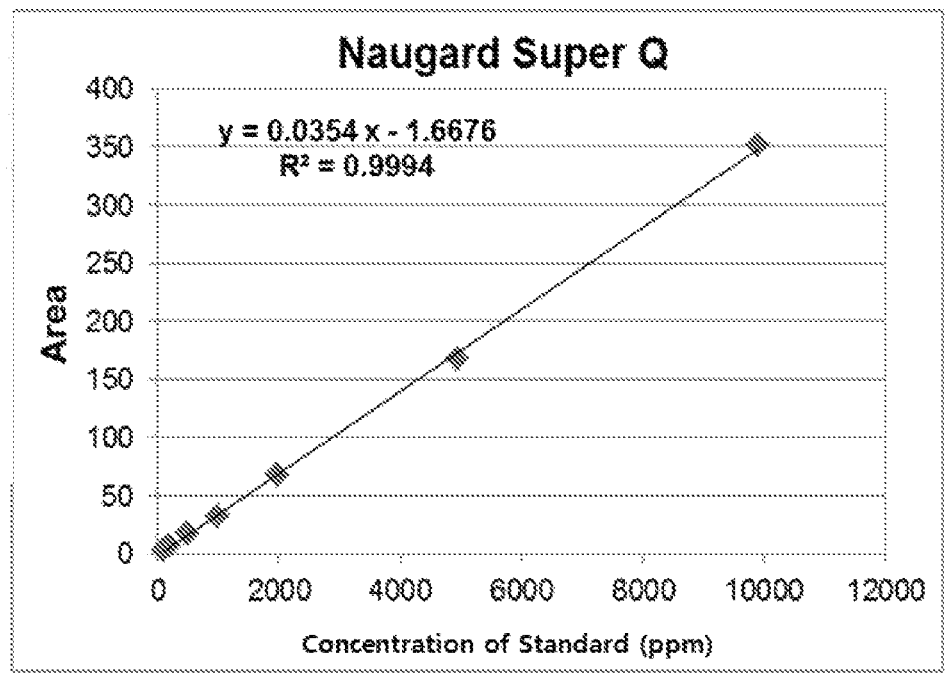

[Fig. 4]
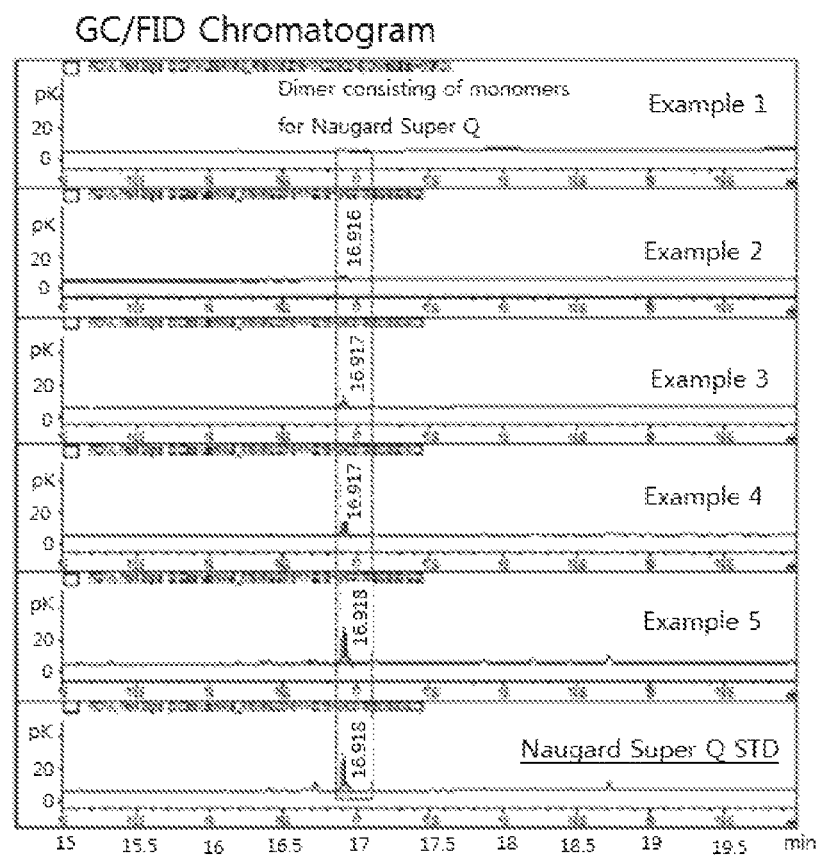

QUANTITATIVE ANALYSIS METHOD FOR HIGH MOLECULAR WEIGHT ANTIOXIDANT

CROSS-REFERENCE TO RELATED APPLICATIONS

The present application is a national phase entry under 35 U.S.C. § 371 of International Application No. PCT/KR2018/008259, filed on Jul. 23, 2018, which claims priority from Korean Patent Application No. 10-2017-0116612, filed on Sep. 12, 2017, all of which are incorporated herein by reference.

BACKGROUND OF THE INVENTION

1. Field of the Invention

The present invention relates to a method for quantitative analysis of high molecular weight antioxidants and, more particularly, to a method for analyzing content of an antioxidant contained in a semiconductive material for a cable, wherein the antioxidant is an amine-based antioxidant.

2. Description of the Related Art

Semiconductive products for insulated power cables for ultra-high voltage or power cables used in power equipment are based on polymer materials. Semiconductive products used in power cables and power equipment should have excellent electrical conductivity due to their usage characteristics, and should not reduce their electrical properties or mechanical properties and should not cause deterioration even after long-term use.

Semiconductive products for cables are produced from a semiconductive composition which is prepared by mixing an ethylene-based copolymer resin, in particular an ethylene-vinyl acetate (EVA) resin, an ethylene-ethyl acrylate (EEA) resin or an ethylene-butyl acrylate (EBA) resin which is used alone or in combination thereof as a matrix resin with carbon black, an antioxidant, a crosslinking agent, a crosslinking aid, a processable lubricant, and the like.

Semiconductive products are subject to a gradual oxidation process due to the effects of temperature, light, and transition metals, if they are not kept in a specific storage condition. Such oxidation typically leads to aging of the polymeric material. The aging of the polymeric material can be significantly reduced by adding an antioxidant.

Naugard Super Q is often used as an antioxidant to improve electrical properties of semiconductive products for cables.

Naugard Super Q (polymerized 1,2-dihydro-2,2,4-trimethylquinoline) is an amine-based antioxidant with molecular weight 874 and has the following formula:

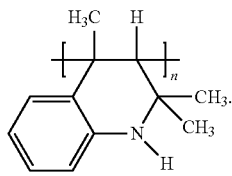

It is an effective long-term heat stabilizer for a variety of application areas in LDPE (low density polyethylene), LLDPE (linear low density polyethylene), HDPE (high density polyethylene) and ethylene-propylene copolymers. It is used in carbon black-filled systems, such as wires and cables. Therefore, it is required to establish quantitative analysis method of Naugard Super Q. Since Naugard Super Q has a polymeric form, it is not detected as a single component in the quantitative analysis by chromatography. It causes a difficulty in the analysis and thus it is necessary to establish an analysis method in order to solve the problem.

The present inventors developed a method for quantitative analysis of the content of Naugard Super Q contained in semiconductive products for cables, by extracting the semiconductive products with an acetone solvent and then analyzing them by gas chromatography (GC)/flame ionization detector (FID).

SUMMARY OF THE INVENTION

It is an object of the present invention to provide a method for accurately analyzing the content of an antioxidant, specifically Naugard Super Q, added to semiconductive products for cables.

Naugard Super Q has a polymeric form, which has been found to be detected not as a single component but as multiple peaks in quantitative analysis with gas chromatography (GC)/mass spectrometry (MS). The same peaks were also detected in analysis with gas chromatography (GC). It is possible to quantify based on the peak of molecular weight (MW) of 362 corresponding to the dimer (dimeric form of monomers having methyl group bonded thereto) consisting of monomers for Naugard Super Q.

In order to achieve the above object, the present invention provides a method for quantitatively analyzing a semiconductive material for a cable containing Naugard Super Q as an antioxidant by GC/FID.

Specifically, the present invention provides a method for quantitatively analyzing a high molecular weight antioxidant in a semiconductive material for a cable, the method comprising the steps of: weighing a semiconductive material for a cable comprising a matrix resin, a high molecular weight antioxidant, carbon black and a crosslinking agent, dissolving the material in an acetone solvent, heating the solution, extracting the solution overnight, cooling the solution to room temperature, filtering it, analyzing filtrate by GC/FID and calculating the content of the antioxidant by using Equation 1 below:

Content of high molecular weight antioxidant (ppm, $\mu g/g$)={$(C_{cal}/W_{sample}) \times V_{sample}$}  [Equation 1], wherein $C_{cal}$ represents concentration (ppm, $\mu g/ml$) of a high molecular weight antioxidant determined using calibration curve; $W_{sample}$ represents weight (g) of a semiconductive sample for a cable; and $V_{sample}$ represents volume (ml) of an acetone solvent.

In one embodiment, the matrix resin comprises an ethylene-vinyl acetate (EVA) resin. In case of a semiconductive material for XLPE cable (cross-linked polyethylene insulated cable), EVA, EEA or EBA resin is used as a basic resin, and LD or LLD wax may be mixed thereto in consideration of properties and workability.

In one embodiment, the matrix resin may be used in an amount of 50 to 60 wt % based on the weight of the semiconductive material for a cable. If the resin content is lower than the lower limit, it is interpreted that the amount of carbon black is relatively increased. In this case, the resistance value of the semiconductive resin becomes higher. Generally, the resistance value of the semiconductive material is controlled to be not more than a specific value (for example, it is controlled to be not more than 1000 Ω·cm at 90° C.). If the resistance value of the semiconductive material is increased, a workability problem such as an increase in the processing load is generally occurred. On the other hand, if the content of the resin is higher than the upper limit, it is interpreted that the amount of carbon black is relatively decreased. It may result in lower mechanical properties and lower productivity of the semiconductive product. In addition, since the amount of carbon black is reduced, the role of electric relaxation may be reduced. Therefore, the ratio of carbon black to matrix resin can be a factor affecting the workability, electrical characteristics, appearance and productivity of semiconductive products.

In one embodiment, the antioxidant comprises Naugard Super Q, an amine-based antioxidant. In one embodiment, the antioxidant is quantifiable in dimeric form of the monomer.

In one embodiment, the semiconductive material for a cable may comprise 50 to 60 wt % of a matrix resin, 0.1 to 1 wt % of an antioxidant, 33 to 40 wt % of carbon black, and 0.3 to 2 wt % of a crosslinking agent. In another embodiment, the semiconductive material for a cable may further comprise additives such as a crosslinking aid and a processing auxiliary, in addition to the above-mentioned components.

In one embodiment, the solution of the semiconductive material for a cable and acetone may be heated to from 50° C. to 60° C.

In one embodiment, the semiconductive material for a cable has a specific resistivity of 500 to 1000 Ω·cm at room temperature and at high temperature (100° C.) in terms of electrical characteristics.

In one embodiment, acetylene black or furnace black may be used as the carbon black. The range of 33 to 40% by weight of the content of the carbon black is such that the workability and mechanical strength are not lowered.

In one embodiment, the crosslinking agent may be at least one selected from the group consisting of dicumyl peroxide (DCP), perbutyl peroxide (PBP), di-tert-butyl peroxydiisopropylbenzene and 1,1-bis(tert-butylperoxy)-3,3,5-trimethyl-cyclohexanol. In another embodiment, triallyl isocyanurate (TAIC) may be used as the crosslinking aid.

In one embodiment, the semiconductive material for a cable may further comprise the crosslinking aid such as ethylene glycol dimethacrylate, 1,3-butylene glycol dimethacrylate or trimethylolpropane trimethacrylate.

In one embodiment, the quantitative analysis value of the antioxidant in the semiconductive material for a cable may be 80% or more relative to the actually used amount.

In one embodiment, the apparatus used for the GC/FID analysis is not particularly limited as long as it is commonly used in the art. For example, an Agilent 5890B GC system of Agilent Technologies (USA) may be used.

Effect of the Invention

According to the quantitative analysis method of the present invention, it is possible to quantitatively analyze a content of a high molecular weight antioxidant by dissolving semiconductive materials for a cable containing a high molecular weight antioxidant in an acetone solvent and analyzing it by GC/FID.

BRIEF DESCRIPTION OF THE DRAWINGS

FIG. 1 shows that quantification is possible based on the peak of molecular weight (MW) of 362 (② M.W. peak) corresponding to the dimer (dimeric form of monomers having methyl group bonded thereto) consisting of monomers for Naugard Super Q.

FIG. 2 shows GC/FID chromatograms for Naugard Super Q standard and Naugard Super Q in the semiconductive material for a cable according to one embodiment of the present invention.

FIG. 3 shows a calibration curve plotted with the concentration of the Naugard Super Q standard and the peak area of the GC/FID chromatogram for the Naugard Super Q.

FIG. 4 shows GC/FID chromatograms for Naugard Super Q standard and Naugard Super Q in each of Examples 1 to 5.

DETAILED DESCRIPTION OF THE INVENTION

Hereinafter, the present invention will be described in more detail.

The terms and words used in the present specification and claims should not be construed as limited to ordinary or dictionary meanings and should be interpreted with the meaning and concept consistent with the technical idea of the present invention based on the principle that the inventor can appropriately define the concept of the term in order to explain his invention in the best way.

An object of the present invention is to provide a method for quantitative analysis of a high molecular weight antioxidant used in semiconductive products, for example Naugard Super Q, for which accurate quantitative analysis was difficult by conventional GC/MS analysis.

In order to achieve the above object, the present invention provides a method for quantitatively analyzing a high molecular weight antioxidant in a semiconductive material for a cable, the method comprising the steps of: weighing a semiconductive material for a cable comprising a matrix resin, a high molecular weight antioxidant, carbon black and a crosslinking agent, dissolving the material in an acetone solvent, heating the solution, extracting the solution overnight, cooling the solution to room temperature, filtering it, analyzing the filtrate by GC/FID and calculating the content of the antioxidant by using Equation 1 below:

$$\text{Content of high molecular weight antioxidant (ppm, } \mu g/g) = \{(C_{cal}/W_{sample}) \times V_{sample}\} \quad \text{[Equation 1]},$$

wherein $C_{cal}$ represents concentration (ppm, μg/ml) of a high molecular weight antioxidant determined using calibration curve; $W_{sample}$ represents weight (g) of a semiconductive sample for a cable; and $V_{sample}$ represents volume (ml) of an acetone solvent.

In one embodiment, the matrix resin is an ethylene-vinyl acetate (EVA) resin. In case of a semiconductive material for XLPE cable, EVA, EEA or EBA resin is used as a base resin, and LD or LLD wax may be mixed thereto in consideration of properties and workability.

In one embodiment, the matrix resin may be used in an amount of 50 to 60 wt % based on the weight of the semiconductive material for a cable. If the resin content is lower than the lower limit, the amount of carbon black is relatively increased and in this case the resistance value of the semiconductive material becomes higher. If the resistance value of the semiconductive material is increased, a workability problem such as an increase in the processing load is occurred. On the other hand, when the content of the resin is higher than the upper limit, it is interpreted that the amount of carbon black is relatively decreased. It may result in lower mechanical properties and lower productivity of the semiconductive product. In addition, since the amount of carbon black is reduced, the role of electric relaxation may be reduced. Therefore, the ratio of carbon black to matrix resin serves as a factor affecting the workability, electrical characteristics, appearance and productivity of semiconductive products.

In one embodiment, the antioxidant comprises Naugard Super Q as an amine-based antioxidant.

In one embodiment, the semiconductive material for a cable may comprise 50 to 60 wt % of a matrix resin, 0.1 to 1 wt % of an antioxidant, 33 to 40 wt % of carbon black, and 0.3 to 2 wt % of a crosslinking agent. In another embodiment, the semiconductive material for a cable may further comprise additives such as a crosslinking aid and a processing auxiliary, in addition to the above-mentioned components.

In one embodiment, the solution of the semiconductive material for a cable and acetone may be heated to from 50° C. to 60° C.

In one embodiment, the semiconductive material for a cable has a resistivity of 500 to 1000 Ω·cm at room temperature and at high temperature (100° C.) in terms of electrical characteristics.

In one embodiment, as the carbon black, acetylene black or furnace black may be used. The range of 33 to 40% by weight of the content of the carbon black is such that the workability and mechanical strength are not lowered.

In one embodiment, the crosslinking agent may be at least one selected from the group consisting of dicumyl peroxide (DCP), perbutyl peroxide (PBP), di-tert-butyl peroxydiisopropylbenzene and 1,1-bis(tert-butylperoxy)-3,3,5-trimethyl-cyclohexanol. In another embodiment, triallyl isocyanurate (TAIC) may be used as the crosslinking aid.

In one embodiment, the semiconductive material for a cable may further comprise the crosslinking aid such as ethylene glycol dimethacrylate, 1,3-butylene glycol dimethacrylate or trimethylolpropane trimethacrylate.

In one embodiment, the quantitative analysis value of the antioxidant in the semiconductive material for the cable may be 80% or more relative to the actually used amount.

In one embodiment, the apparatus used for the GC/FID analysis is not particularly limited as long as it is commonly used in the art. For example, an Agilent 5890B GC system of Agilent Technologies (USA) may be used.

Hereinafter, embodiments of the present invention will be described in detail so that those skilled in the art can easily carry out the present invention. The present invention may, however, be embodied in many different forms and should not be construed as limited to the embodiments set forth herein.

Example

1. Preparation of Sample
1) 1 g of semiconductive pellets (including EVA resin) for a cable were precisely weighed into 15 ml vials, added 10 ml of acetone thereto and extracted the solution overnight at 60° C.
2) The solution obtained from 1) above was cooled to room temperature, filtered the solution, and analyzed the filtrate by GC/FID.

2. Analysis Condition of GC/FID
An Agilent 5890B GC system from Agilent Technologies, Inc. was used for GC/FID analysis.

The column was HP-5. The GC oven temperature was maintained at 100° C. for 3 minutes. Then, the temperature was raised to 320° C. at a rate of 15° C./min and then maintained for 20 minutes at the same temperature to obtain a chromatogram (total operation time: 38 minutes). The detailed analysis condition is as follows.

Column: HP-5 (30 m L.×0.32 mm I.D., 0.25 μm d.f. capillary)
Gas flow rate: Column (He): 1 mL/min
Oven temperature: 100° C., 3 min→15° C./min→320° C., 20 min
Injection volume: 1.0 μL
Injector Split ratio: 20/1

3. Chromatogram of Standard Solution
The Naugard Super Q standard solution was detected as several peaks, and the retention time of the dimer was 16.9 minutes as shown in FIG. 2.

4. Calculation of Content of Naugard Super Q
(1) Peaks on the GC/FID chromatogram for Naugard Super Q standard solution were identified and the areas of the peaks were calculated. The calibration curve was obtained by plotting the concentration of the standard solution and the calculated peak area. The correlation coefficient ($R^2$) should be not less than 0.995. The calibration curve is shown in FIG. 3.

(2) Peaks on the chromatogram for the sample solution were identified and the areas of the peaks were calculated. Then the concentration was obtained by using the calibration curve. The concentration of Naugard Super Q in the sample was calculated according to Equation 1 below:

$$\text{Content of high molecular weight antioxidant (ppm, μg/g)} = \{(C_{cal}/W_{sample}) \times V_{sample}\} \quad \text{[Equation 1]},$$

wherein $C_{cal}$ represents concentration (ppm, μg/ml) of a high molecular weight antioxidant determined using calibration curve; $W_{sample}$ represents weight (g) of a semiconductive sample for a cable; and $V_{sample}$ represents volume (ml) of an acetone solvent.

In this experiment, the volume of acetone solvent was 10 ml. That is, the sample was extracted by using 10 ml of acetone as a pretreatment solvent ($V_{sample}$=10 ml).

Examples 1 to 5

(1) Purpose
The purpose is to perform quantitative analysis of different contents of Naugard Super Q contained in semiconductive materials (to confirm the accuracy of quantitation by checking the difference between the prescription value (the actually used amount) and the measurement value).

(2) Preparation of Sample
Five samples (corresponding to Examples 1 to 5, respectively) were prepared as described in the "1. Preparation of sample" above by using semiconductive pellets for a cable having different contents of Naugard Super Q, and then analyzed the samples by GC/FID. Then, the contents of Naugard Super Q in the samples were determined three times for each sample by using Equation 1 above to obtain an average value of the measurement values.

(3) Results
The results of measurement of the content of Naugard Super Q in each of the semiconductive materials of Examples 1 to 5 were analyzed with an average recovery rate of 90% to the prescription values (the actually used amount). The prescription values and the measurement values of the content of Naugard Super Q are shown in Table 1 below. The GC/FID chromatogram for each of the samples of Examples 1 to 5 is shown in FIG. 4. From FIG. 4, it can be seen that the retention time of the dimeric form of monomers for Naugard Super Q for each of the samples of Examples 1 to 5 is 16.9 minutes which is similar to that in the GC/FID chromatogram for the Naugard Super Q standard of FIG. 2

TABLE 1

| Sample of semiconductive material | Prescription value (wt %) | Measurement value (wt %) | Ratio of Measurement value to Prescription value (%) | Average ratio of Measurement value to Prescription value (%) |
|---|---|---|---|---|
| Example 1 | N/A | — | — | 90.0 |
| Example 2 | 0.1 | 0.08 | 80.0 | |
| Example 3 | 0.3 | 0.28 | 93.3 | |
| Example 4 | 0.5 | 0.45 | 90.0 | |
| Example 5 | 1.0 | 0.96 | 96.0 | |

Based on the results shown in Table 1, it can be seen that according to the present invention it is possible to accurately measure the content of the high molecular weight antioxidant in the semiconductive material with respect to the actually used amount.

While the present invention has been particularly shown and described with reference to specific embodiments thereof, it will be apparent to those skilled in the art that this specific description is merely a preferred embodiment and that the scope of the invention is not limited thereby. It is therefore intended that the scope of the invention be defined by the claims appended hereto and their equivalents.

What is claimed is:

1. A method for quantitative analysis of an antioxidant in a semiconductive material for a cable:
    weighing the semiconductive material, wherein the semiconductive material comprises a matrix resin, a high molecular weight antioxidant, carbon black and a crosslinking agent,
    dissolving the semiconductive material in an acetone solvent to form the solution,
    heating the solution,
    extracting the solution overnight,
    cooling the solution to room temperature,
    filtering the solution to form a filtrate,
    analyzing the filtrate by gas chromatography (GC)/flame ionization detector (FID) and calculating a content of the antioxidant by using Equation 1 below to provide an quantitative analysis value of the antioxidant in the semiconductive material:

Content of high molecular weight antioxidant(ppm, µg/g)={$(C_{cal}/W_{sample}) \times V_{sample}$}  [Equation 1], wherein $C_{cal}$ represents a concentration (ppm, µg/ml) of the high molecular weight antioxidant determined by using calibration curve;

$W_{sample}$ represents a weight (g) of a the semiconductive material; and $V_{sample}$ represents a volume (ml) of the acetone solvent,
    wherein the antioxidant is an amine-based antioxidant, Naugard Super Q (polymerized 1,2-dihydro-2,2,4-trimethylgyinoline).

2. The method according to claim 1, wherein
    the matrix resin is present in an amount from 50 wt % to 60 wt % based on a total weight of the semiconductive material,
    the antioxidant is present in an amount from 0.1 wt % to 1 wt % based on a total weight of the semiconductive material,
    the carbon black is present in an amount from 33 wt % to 40 wt % based on a total weight of the semiconductive material, and
    the crosslinking agent is present in an amount from 0.3 wt % to 2 wt % based on a total weight of the semiconductive material.

3. The method according to claim 1, wherein the matrix resin comprises an ethylene-vinyl acetate (EVA) resin.

4. The method according to claim 1, wherein the solution of the semiconductive material is heated to a temperature ranging from 50° C. to 60° C.

5. The method according to claim 1, wherein the quantitative analysis value of the antioxidant in the semiconductive material is 80% or more relative to an actual amount used.

6. The method according to claim 1, wherein the crosslinking agent is dicumyl peroxide (DCP), perbutyl peroxide (PBP), di-tert-butyl peroxydiisopropylbenzene or 1,1-bis(tert-butylperoxy)-3,3,5-trimethyl-cyclohexanol.

* * * * *